United States Patent [19]
Jacobi

[11] Patent Number: 5,443,507
[45] Date of Patent: Aug. 22, 1995

[54] INTRAOCULAR LENS SET

[75] Inventor: Karl W. Jacobi, Giessen, Germany

[73] Assignee: adatomed Pharmazeutische und medizintechnische Gesellschaft mbH, Munich, Germany

[21] Appl. No.: 41,582

[22] Filed: Apr. 5, 1993

[30] Foreign Application Priority Data

Apr. 3, 1992 [EP] European Pat. Off. ........... 92105814

[51] Int. Cl.⁶ .............................................. A61F 2/16
[52] U.S. Cl. .................... 623/6; 351/160 R; 351/161
[58] Field of Search ............... 623/5, 6; 351/160 R, 351/161

[56] References Cited

U.S. PATENT DOCUMENTS

| | | | |
|---|---|---|---|
| 4,655,565 | 4/1987 | Freeman | 623/6 X |
| 4,923,296 | 5/1990 | Erickson | 623/6 X |
| 5,089,023 | 2/1992 | Swanson | 623/6 |
| 5,089,024 | 2/1992 | Christie et al. | 623/6 |
| 5,096,285 | 3/1992 | Silberman | 351/161 |
| 5,151,723 | 9/1992 | Tajiri | 351/160 R X |
| 5,178,636 | 1/1993 | Silberman | 623/6 |
| 5,245,366 | 9/1993 | Svochak | 351/161 |

FOREIGN PATENT DOCUMENTS

| | | |
|---|---|---|
| 0140063 | 5/1985 | European Pat. Off. . |
| 0453136 | 10/1991 | European Pat. Off. . |
| 4134518 | 4/1993 | Germany . |
| WO89/02251 | 3/1989 | WIPO . |
| WO90/00889 | 2/1990 | WIPO . |
| WO91/09336 | 6/1991 | WIPO . |

*Primary Examiner*—Mary Beth O. Jones
*Attorney, Agent, or Firm*—Keck, Mahin & Cate

[57] ABSTRACT

An intraocular lens set includes at least two multifocal intraocular lenses. The first lens of this set has at its far focus a higher proportion of light distribution than the second lens. The second lens has at its near focus a higher proportion of light distribution than the first lens.

2 Claims, 5 Drawing Sheets

LEFT  RIGHT

INTRAOCULAR LENS SET

BACKGROUND OF THE INVENTION

The present invention concerns an intraocular lens set comprising at least two multifocal intraocular lenses.

When multifocal intraocular lenses are used, for example, for the treatment of cataracts, a lower level of sensitivity in terms of contrast has to be accepted. That can give rise to difficulties, in particular, for example, when driving a motor vehicle at night. When using intraocular lenses having a central lens region for near vision and a lens region surrounding the central lens region, for distance vision, there is also a high level of dependency of the amount of light which is incident through the respective part of the lens on the pupil size.

SUMMARY OF THE INVENTION

An object of the present invention is to provide an intraocular lens set which affords enhanced contrast sensitivity and improved vision under reduced light conditions such as in twilight or at night.

In accordance with the principles of the present invention, the foregoing and other objects are achieved by a combination lens set comprising at least first and second multifocal intraocular lenses wherein, in a combination of two intraocular lenses of the set, the first lens, for its far focus, has a higher proportion of the total light distribution passing through that lens than the second lens, and the second lens, for its near focus, has a higher proportion of the light distribution passing through that lens, than the first lens.

In a preferred feature of the invention, the higher proportion of light distribution for the far focus and the near focus, respectively, in regard to each of the first and second intraocular lenses of said combination, is between about 60% and 70% of the total light distribution passing through the respective lens.

Another preferred feature of the invention provides that the two intraocular lenses can be in the form of substantially bifocal lenses. They may be lenses which are in the form of a refractive lens at their one surface side and a dispersion lens at their other surface side. The strength or intensity of the light at the respective focal point, being either the far vision focus or the near vision focus, of the respective lens, can thus be enhanced by the dispersion effect, that is to say by interference of in-phase light waves. In this respect, attention may be directed to German patent application No. P41 34 518.5) to which reference may accordingly be made for fuller details in this respect. However the lenses may also be of the design configuration disclosed in EP 0 140 063 B1, in which case, to achieve the higher proportion of light distribution passing through the lens, correspondingly more lens regions for the near vision viewing range and the far vision viewing range, respectively, are provided on the respective lens body.

Further objects, features and advantages of the present invention will be apparent from the following description.

DESCRIPTION OF THE PREFERRED EMBODIMENT

Figure 1:
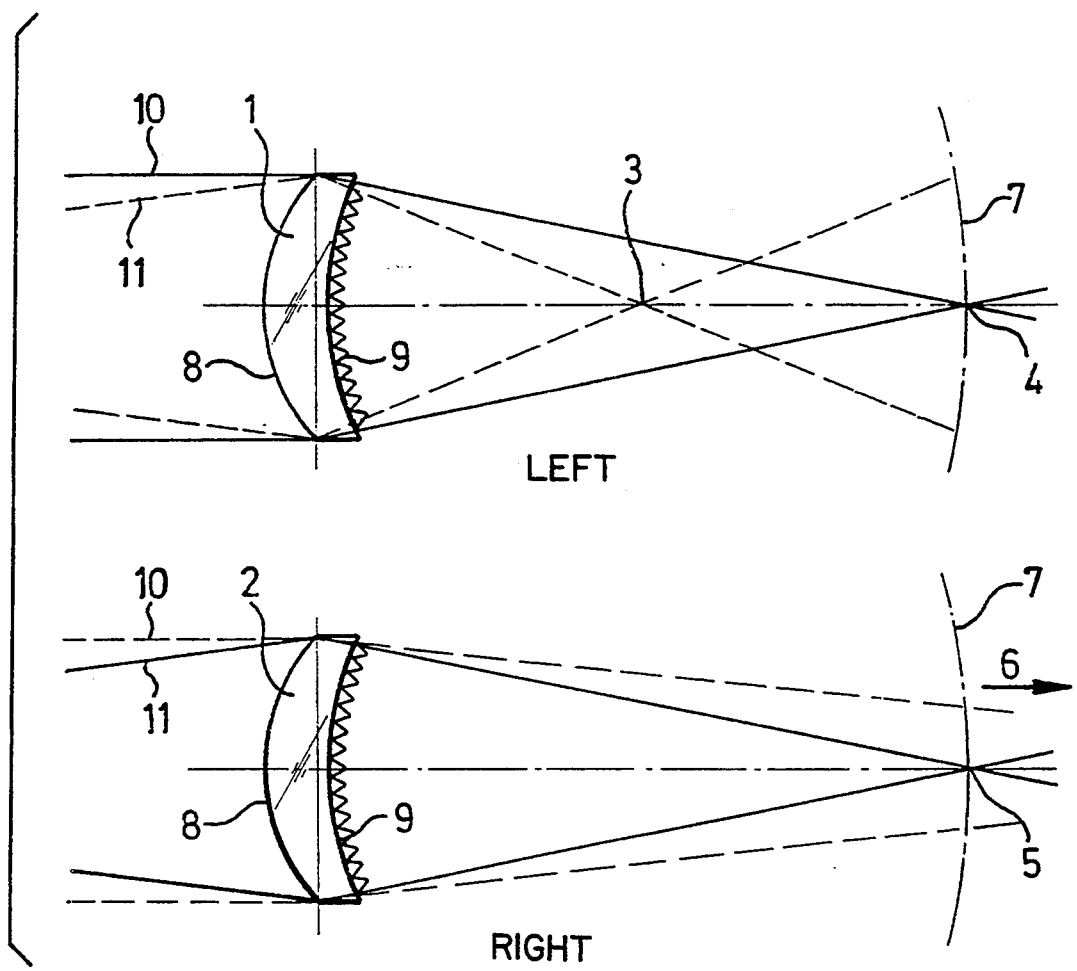
FIG. 1 is a diagrammatic view of first and second bifocal intraocular lenses of an intraocular lens set with the associated far vision and near vision focal lengths with asymmetric light distribution on to the far vision and near vision ranges of the respective lens.

Referring firstly to FIG. 1, shown therein are first and second bifocal intraocular lenses 1 and 2 which form an intraocular lens set in accordance with an embodiment of the present invention.

The intraocular lens 1 has a far vision focus 4 at which parallel light rays 10 coming from far are focussed. Light rays 11 which are incident on the eye from near are focussed at a near vision focus 3. The dash-dotted line indicated at 7 identifies the retina of the eye in which the respective intraocular lens is implanted.

The incident light energy is focussed with a greater proportion, for example between 60% and 70%, at the far vision focus 4 than the near vision focus 3. It will be seen that, when the lens is in the implanted condition, the far vision focus 4 is on the retina of the eye as indicated at 7. The proportion of light distribution at the near vision focus 3 is thus for example between abut 30% and 40%.

The light which is collected at the far vision focus 4 on the retina 7 of the eye thus produces a sharp image on the retina of the eye. The strength or intensity of the focussed light coming from a far range in front of the eye having the implanted intraocular lens 1 considerably exceeds the strength or intensity of the light which comes from near and which is out-of-focus on the retina 7. That light which is coming from near produces on the retina 7 an only extremely weak unstructured image. Thus, referring to FIG. 2, in regard to the intraocular lens 1, which is the lens implanted in a left eye, shown therein is the light whose image is formed at the far vision focus 4 and the light whose image is formed by the near vision focus 3. For the image (E) coming from far, the lens provides image formation which affords good sharpness and good contrast while the near image involves a lower degree of strength or intensity, corresponding to the lower contribution to light distribution afforded by the lens 1 in respect of its near vision focus.

Still looking at FIG. 1, the intraocular lens set has the second intraocular lens 2 whose near vision focus 5, in the implanted condition, is on the retina of the eye, as indicated by the dash-dotted line 7. In the case of the intraocular lens 2, a larger proportion, for example between about 60% and 70%, of the light energy which passes through the intraocular lens 2 is focussed at the near vision focus 5 than at the far vision focus 6 which is thus behind the retina 7. The light 11 which is incident on the intraocular lens 2 from near is collected at the near vision focus 5. The light 10 from far, which is incident on the intraocular lens 2 in the form of parallel rays would be focussed at the far vision focus 6.

Figure 2:
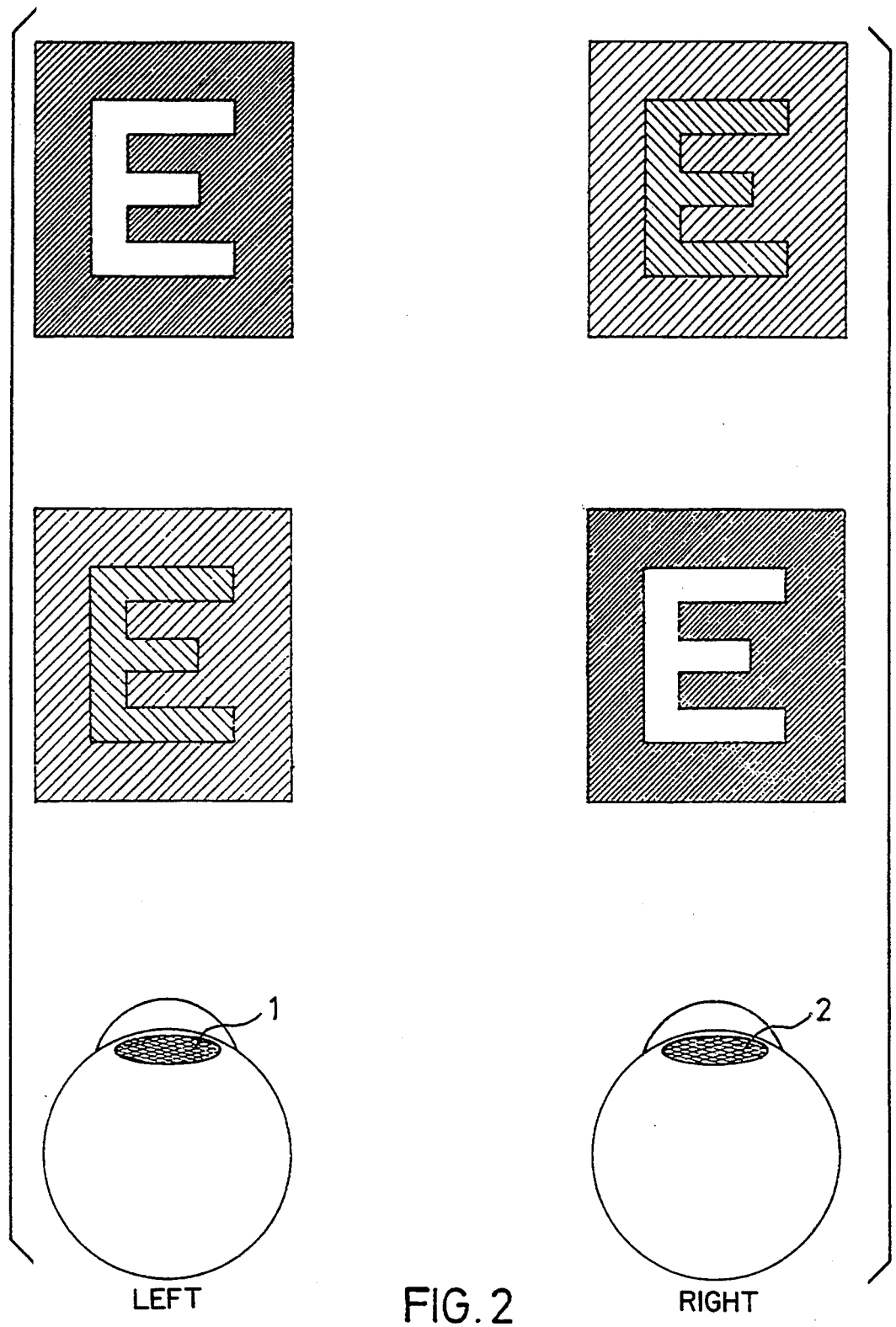
FIG. 2 is a view of the respective lenses in the near vision and the far vision ranges.

As shown in FIG. 2, a sharp image of the near range is formed by the near vision focus 5 of the lens 2, which is the lens implanted in the right eye, while a relatively low-intensity image which corresponds to the lower proportion of light distribution is formed in respect of the far range.

Figure 3:
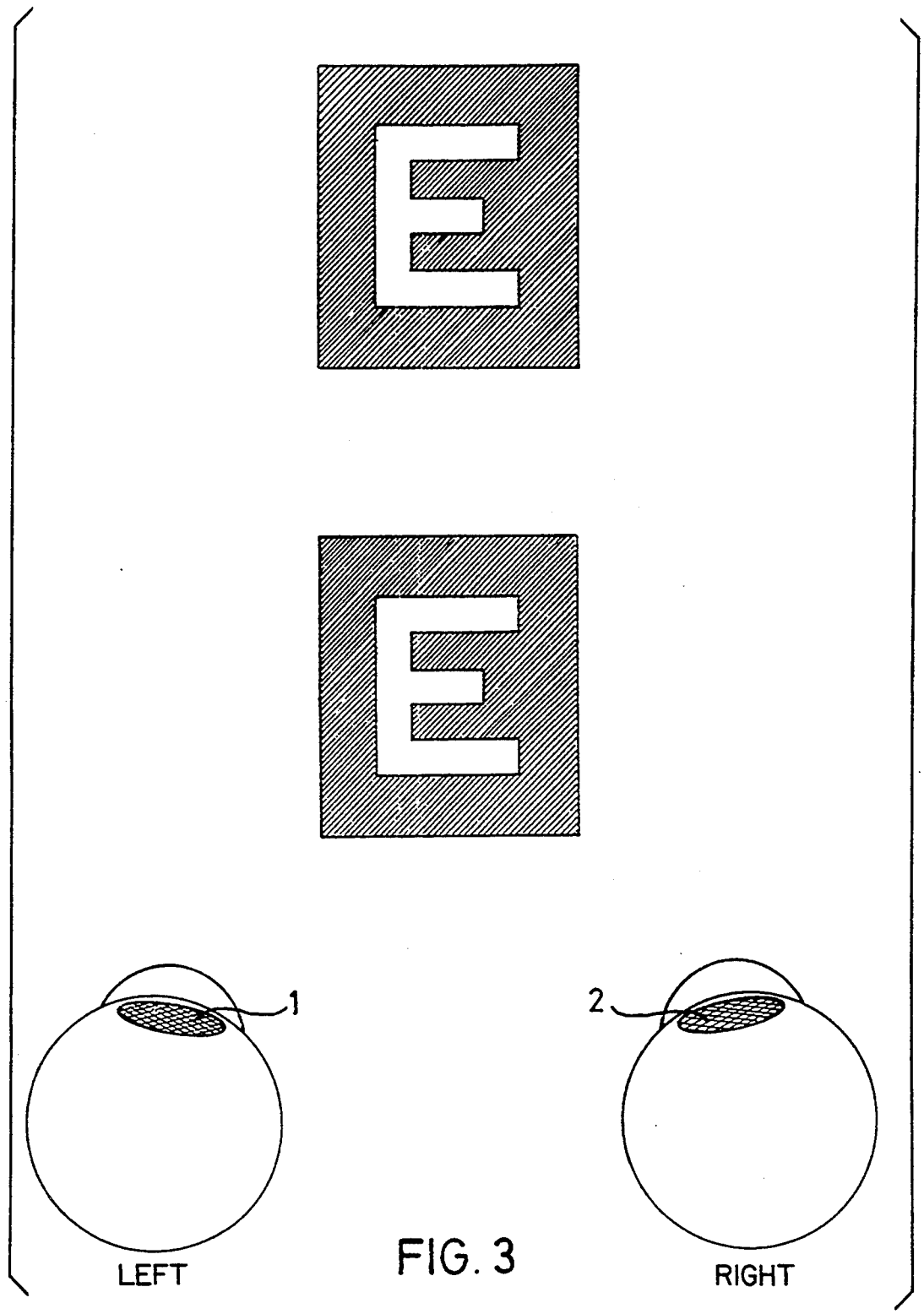
FIG. 3 shows the combinational co-operation of the lenses.

Reference can now be made to FIG. 3 from which it can be clearly seen that sharp high-contrast images with high levels of strength and intensity can be produced by virtue of the combinational co-operation of the two implanted intraocular lenses 1 and 2, both for far vision and for close vision.

For the purposes of checking the visual capabilities when using an intraocular lens set in accordance with an embodiment of the invention, the defocussing curves of two intraocular lenses were investigated. The one intraocular lens, being the lens for the right eye, has a proportion of light distribution of about 60%, in respect of the near vision focus, and a proportion of about 40%, for the far vision focus. The other intraocular lens, intended for the left eye, has a proportion of light distribution of about 40% in respect of the near vision focus and a proportion of about 60% in respect of the far vision focus.

Figure 4:
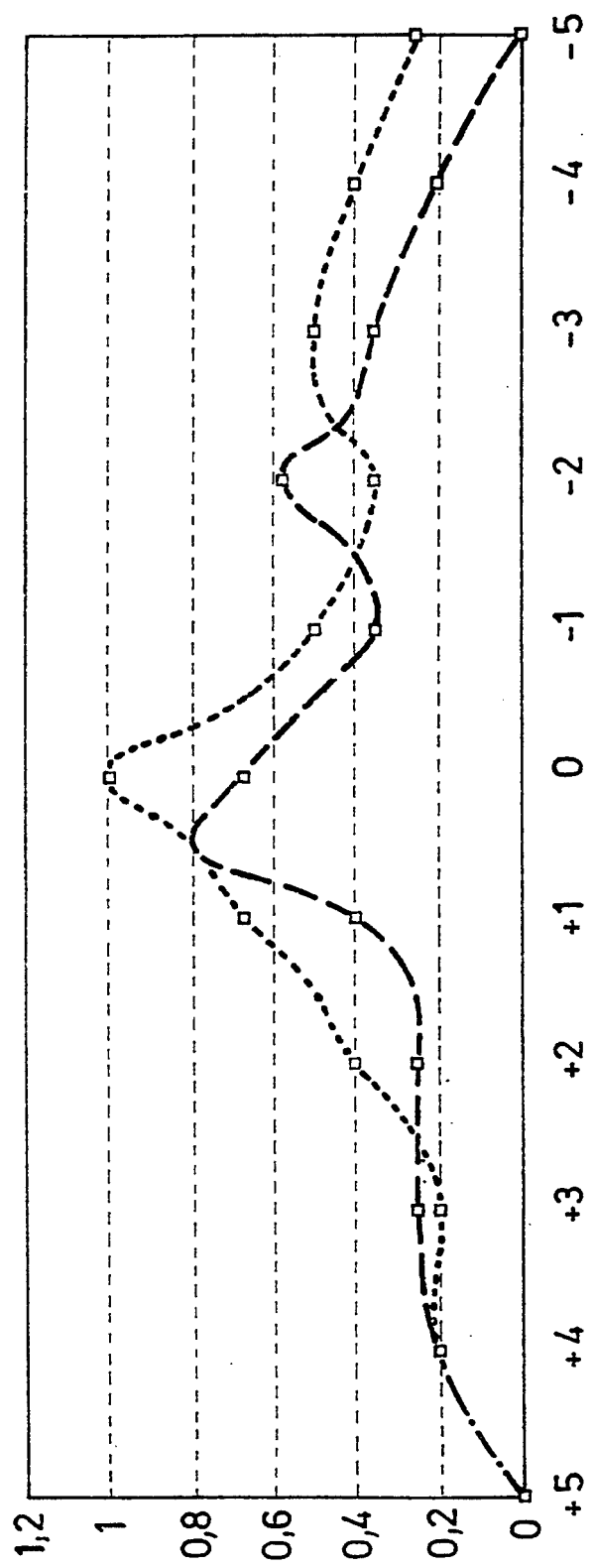
FIG. 4 shows a contrast sensitivity diagram at various distances in accordance with Regan for two bifocal intraocular lenses forming a component of an embodiment of the invention.
Figure 5:
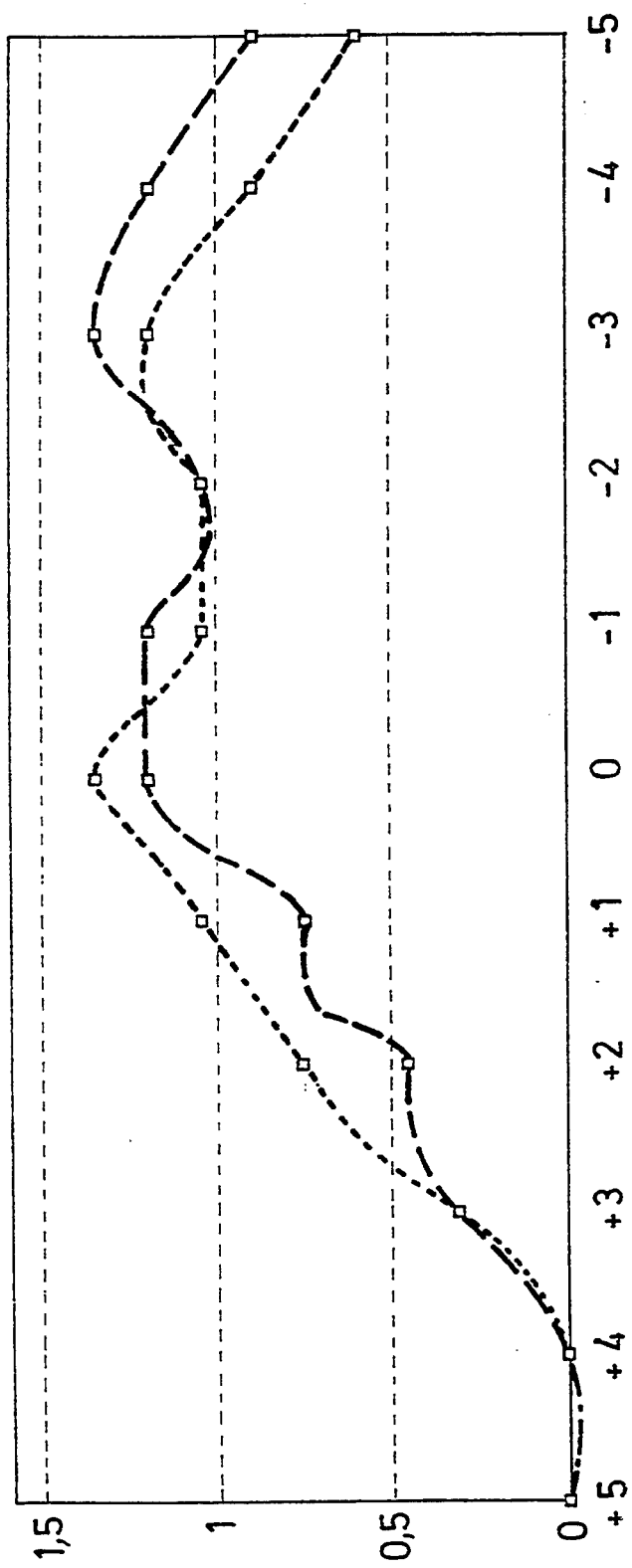
FIG. 5 shows a contrast sensitivity diagram at different distances in accordance with Pelli-Robson for two bifocal intraocular lenses which are a component of an embodiment of the invention.

FIG. 4 shows in respect of the two lenses the defocussing curves for visual acuity or resolving power in accordance with Regan 96%. FIG. 5 shows the defocussing curves for the two lenses in respect of vision contrast in accordance with Pelli-Robson.

The two lenses used in an intraocular lens set may be such that their refractive power is composed of a diffractive and a refractive component. Such intraocular lenses are described in above-mentioned German patent application No. P 41 34 518.5 to which reference is accordingly directed. In such lenses, the refractive power of the refractive lens portion may also have added thereto the additional diffractive power so that one of the two foci is suppressed to a corresponding extent. A sawtooth profile may be used for the diffractive fine structure at the rear side as indicated at 9 in FIG. 1 in respect of the lens 1 or the lens 2, in which case the profile height or the difference in respect of the optical wavelength between highest and lowest points in the design wavelength preferably corresponds to a wavelength in the green spectral region of visible light. In that case, the effect of the diffractive fine structure profile at the rear 9 of the lens 1 or the lens 2 can be so adjusted that the lens approximates to the effect of a monofocal lens. The refractive portion of each of the lenses 1 and 2 is formed at the front side thereof as indicated at 8 in FIG. 1.

It will be appreciated that the above-described lens set according to the present invention has been set forth only by way of example and illustration thereof and that various other modifications may be made therein without thereby departing from the spirit and scope of the invention.

What is claimed is:

1. An intraocular lens set comprising:

first and second intraocular lenses, each having a front side, a rear side, a far vision focus, a near vision focus, a refractive power and a diffractive power, and a diffractive structure, providing the diffractive power, disposed on the rear side of each of the lenses, a profile height of the diffractive structure consisting of a profile height corresponding to a wavelength in the green spectral region of visible light, the diffractive and the refractive powers being added such that the far vision focus of the first intraocular lens has a higher contribution to a total light distribution passing through the first lens than the second lens and the near vision focus of the second intraocular lens has a higher contribution to the total light distribution passing through the second lens than the first lens.

2. A set as set forth in claim 1 wherein each said higher contribution is between 60% and 70% of the total light distribution.

* * * * *